(12) United States Patent
Lee et al.

(10) Patent No.: US 8,415,967 B2
(45) Date of Patent: Apr. 9, 2013

(54) WAFER INSPECTION APPARATUS

(75) Inventors: Yeu Yong Lee, Seoul (KR); Jung-Jae Im, Gunpo-Si (KR)

(73) Assignee: Chang Sung Ace Co., Ltd., Gyeonggi-Do (KR)

( * ) Notice: Subject to any disclaimer, the term of this patent is extended or adjusted under 35 U.S.C. 154(b) by 483 days.

(21) Appl. No.: 12/837,279

(22) Filed: Jul. 15, 2010

(65) Prior Publication Data

US 2011/0013013 A1 Jan. 20, 2011

(30) Foreign Application Priority Data

Jul. 17, 2009 (KR) .................. 10-2009-0065496
Jul. 17, 2009 (KR) .................. 10-2009-0065502

(51) Int. Cl.
*G01R 31/02* (2006.01)

(52) U.S. Cl.
USPC .............. 324/762.05; 324/757.03; 324/758; 324/718; 365/237.1; 365/237.2; 365/237.3; 73/865

(58) Field of Classification Search ............ 324/762.05, 324/757.03, 758, 718, 97; 356/237.1–237.3; 73/865
See application file for complete search history.

(56) References Cited

U.S. PATENT DOCUMENTS

| | | | | |
|---|---|---|---|---|
| 6,137,303 A | * | 10/2000 | Deckert et al. | 324/757.03 |
| 6,259,960 B1 | * | 7/2001 | Inokuchi | 700/110 |
| 2002/0191167 A1 | * | 12/2002 | Aoki | 355/53 |
| 2003/0029220 A1 | * | 2/2003 | Isozaki et al. | 73/1.01 |
| 2003/0159528 A1 | * | 8/2003 | Kim et al. | 73/865.8 |
| 2004/0163670 A1 | * | 8/2004 | Ko et al. | 134/2 |
| 2008/0124206 A1 | * | 5/2008 | Choi et al. | 414/744.2 |

FOREIGN PATENT DOCUMENTS

| | | |
|---|---|---|
| JP | 2003-065727 | 3/2003 |
| KR | 10-2004-0067908 | 7/2004 |

* cited by examiner

*Primary Examiner* — Huy Q Phan
*Assistant Examiner* — Thang Le
(74) *Attorney, Agent, or Firm* — IPLA P.A.; James E. Bame

(57) ABSTRACT

A wafer inspection apparatus that performs surface inspection and internal inspection of solar cells using a single apparatus. The wafer inspection apparatus includes a loading unit configured to allow a cassette to be lifted up or lowered by an elevator. A surface inspection unit includes a plurality of stages, thus performing surface inspection of each wafer using a first vision module. A wafer transfer unit has a rotatably installed center portion and has both ends provided with adsorption parts. An internal inspection unit is configured such that a conveyor is installed to allow the wafer to be transferred, thus performing internal inspection of the transferred wafer through a second vision module. An unloading unit enables wafers having completed the internal inspection to be sequentially loaded onto the unloading unit. A control unit controls a series of wafer inspection procedures.

14 Claims, 17 Drawing Sheets

(a)

(b)

(a)　　　　　　　　　　(b)

WAFER INSPECTION APPARATUS

CROSS REFERENCE

This application claims foreign priority under Paris Convention and 35 U.S.C. §119 to Korean Patent Application No. 10-2009-0065502, filed Jul. 17, 2009 and Korean Patent Application No. 10-2009-0065496, filed Jul. 17, 2009 with the Korean Intellectual Property Office.

BACKGROUND OF THE INVENTION

1. Technical Field

The present invention relates, in general, to a wafer inspection apparatus, and, more particularly, to a wafer inspection apparatus that can successively perform surface inspection and internal inspection of solar cells using a single apparatus.

2. Description of the Related Art

Generally, a solar cell is a device which converts sunlight into electrical energy using the properties of semiconductor. Recently, solar cells have been used for the auxiliary power sources of mobile information devices such as mobile phones or Personal Digital Assistants (PDAs), the drive power sources of transportation means such as vehicles, the generation of electricity, and the supply of hot water. At present, as a method of obtaining high electric power, research into solar cell modules in which multiple solar cells are connected in series or parallel and configured to realize small size and generate high power has been actively conducted.

Such a solar cell (hereinafter referred to as a 'wafer') undergoes surface and internal inspections, that is, essential inspections such as inspections of cell uniformity, hot spots, array non-uniformity, and surface contamination levels during a manufacturing process. Such surface and internal inspections are conducted by independent inspection apparatuses, respectively. That is, those inspections are performed in such a way that after surface inspection of wafers has been completed by a surface inspection apparatus, an operator lifts up a wafer cassette and transfers it to another inspection apparatus, and then enables internal inspection of wafers to be performed.

However, a series of operations for inspecting wafers as described above are mainly separated independently in a main production line, so that operation connectivity is deteriorated, and thus production efficiency is decreased.

FIG. 12 is a plan view showing the structure of a conventional wafer inspection apparatus.

Referring to FIG. 12, a conventional wafer inspection apparatus 1a is configured such that multiple wafers W are loaded onto and transferred along a conveyor 10a, which is supplied with power from a motor (not shown) and is then rotated, by a wafer transfer robot (not shown), and such that an articulated robot 13a installed above the conveyor 10a adsorptively transfers the transferred wafers W one by one, places the wafers W on the stage 21a of an inspection device 20a provided on a portion of the wafer inspection apparatus, performs inspection on the wafers W, and places wafers W having completed the inspection back on the conveyor 10a.

However, such inspection apparatuses 1a are problematic because they are independently separated in a main production line, thus deteriorating connectivity in manufacturing processes, and because inspection is performed on multiple wafers W by transferring the wafers W one by one, thus taking a great deal of time to inspect wafers W using this method.

Further, there is inconvenience in that in order to perform such an inspection process, an operator must personally lift up and transfer a cassette (not shown) with wafers W loaded therein, and there is a problem in that wafers W may be damaged or contaminated with particles due to the carelessness of an operator during the process of transferring the cassette.

SUMMARY OF THE INVENTION

Accordingly, the present invention has been made keeping in mind the above problems occurring in the prior art, and an object of the present invention is to provide a wafer inspection apparatus, which can successively perform surface inspection and internal inspection of wafers using a single apparatus, and can simultaneously inspect a large number of wafers, thus improving working efficiency.

In order to accomplish the above object, the present invention provides a wafer inspection apparatus, comprising a loading unit configured to allow a cassette, in which multiple wafers are loaded, to be lifted up or lowered by an elevator, the loading unit having push means installed on a portion thereof to allow the wafers to be horizontally withdrawn one by one; a surface inspection unit provided with a plurality of stages on a top surface thereof so that the wafers withdrawn from the loading unit can be loaded onto the stages, the surface inspection unit performing surface inspection of each of the wafers using a first vision module installed above the stages; a wafer transfer unit, a center portion of which is rotatably installed and both ends of which are provided with adsorption parts so as to adsorptively fix a top surface of each wafer having completed the surface inspection and transfer the wafer to a subsequent process; an internal inspection unit in which a conveyor that is rotated in one direction by power supplied from a motor is installed to allow the wafer transferred by the wafer transfer unit to be transferred, the internal inspection unit performing internal inspection of the transferred wafer through a second vision module installed above and below the conveyor; an unloading unit located closer to an end portion of the conveyor in a transfer direction thereof, and provided with a cassette lifted up or lowered by an elevator, thus enabling wafers having completed the internal inspection to be sequentially loaded onto the unloading unit; and a control unit configured to control a series of wafer inspection procedures in compliance with sequential control programming.

Preferably, the push means may comprise an air cylinder, and a push rod coupled to inside of the air cylinder to be forwardly and backwardly movable and provided with a horizontal reciprocating element coupled to a front end of the push rod.

Preferably, the surface inspection unit may comprise a rotatable table installed to be rotatable by power supplied from the motor, and provided with at least four stages installed to be spaced apart from one another by a predetermined angle around a shaft so that wafers can be loaded onto top surfaces of the stages; the first vision module including a camera installed above the rotatable table independent of the rotatable table, and surface inspection lighting elements installed on both sides of the camera; and a first discharge unit formed to be downwardly inclined below the stages so that a wafer determined by the first vision module to be defective can be separately discharged.

Preferably, each of the stages may comprise supports for supporting both ends of a wafer and an air cylinder for moving the supports away from each other in opposite directions.

Preferably, the internal inspection unit may comprise the conveyor rotated in one direction by power supplied from a motor so that each wafer transferred by the wafer transfer unit can be transferred; the second vision module provided with a camera and an internal inspection lighting element respectively installed above and below the conveyor so that internal inspection of the wafer transferred by the conveyor can be performed; and a second discharge unit, a first end of which is coupled to a hinge axis in a longitudinal direction of the conveyor, the second discharge unit being downwardly rotated by a predetermined angle around the hinge axis as a center of rotation by way of an operating cylinder installed on a portion of the second discharge unit.

Preferably, the conveyor for which the second vision module is installed may have a predetermined separation space formed therein so that the camera and the internal inspection lighting element can see through the wafer.

Preferably, the internal inspection unit may include a blackout curtain installed therein to shut out incoming light and darken the internal inspection unit.

Further, the present invention provides a wafer inspection apparatus, comprising a loading unit configured to allow a cassette, in which multiple wafers are loaded, to be lifted up or lowered by an elevator, the loading unit having a push rod installed on a portion thereof to allow the wafers to be horizontally withdrawn one by one; a surface inspection unit provided with a plurality of stages on a top surface thereof so that the wafers withdrawn from the loading unit can be loaded onto the stages, the surface inspection unit performing bending deformation inspection of each of the wafers while performing surface inspection of the wafer using a first vision module installed above the stages; a wafer transfer unit, a center portion of which is rotatably installed and both ends of which are provided with adsorption parts so as to adsorptively fix a top surface of each wafer having completed the surface inspection and transfer the wafer to a subsequent process; an internal inspection unit in which a conveyor, which is rotated in one direction by power supplied from a motor, is installed to allow the wafer transferred by the wafer transfer unit to be transferred, the internal inspection unit performing internal inspection of the transferred wafer through a second vision module installed above and below the conveyor; an unloading unit located closer to an end portion of the conveyor in a transfer direction thereof, and provided with a cassette lifted up or lowered by an elevator, thus enabling wafers having completed the internal inspection to be sequentially loaded onto the unloading unit; and a control unit configured to control a series of wafer inspection procedures in compliance with sequential control programming.

Preferably, the surface inspection unit may comprise a rotatable table installed to be rotatable by power supplied from the motor, and provided with at least four stages installed to be spaced apart from one another by a predetermined angle around a shaft so that wafers can be loaded onto top surfaces of the stages; the first vision module including a camera installed above the rotatable table independent of the rotatable table, and surface inspection lighting elements installed on both sides of the camera; a laser measurement unit located adjacent to the first vision module, and provided with a laser measurement element, which is installed to be perpendicular to a wafer and is configured to radiate a laser beam onto the wafer, and a sensor head, to which the radiated laser beam returns, thus measuring a bending deformation degree of the wafer; and a first discharge unit formed to be downwardly inclined below the stages so that a wafer determined by the first vision module or the laser measurement unit to be defective can be separately discharged.

Further, the present invention provides a wafer inspection apparatus, comprising a loading unit configured to allow multiple wafers to be transferred by a first conveyor; a surface inspection unit provided with a plurality of stages on a top surface thereof so that the wafers transferred by the loading unit can be loaded onto the stages, the surface inspection unit performing surface inspection of each of the wafers using a first vision module installed above the stages; a wafer transfer unit, a center portion of which is rotatably installed and both ends of which are provided with adsorption parts so as to adsorptively fix a top surface of each wafer having completed the surface inspection and transfer the wafer to a subsequent process; an internal inspection unit in which a conveyor that is rotated in one direction by power supplied from a motor is installed to allow the wafer transferred by the wafer transfer unit to be transferred, the internal inspection unit including a second vision module installed above and below the conveyor to perform an internal inspection of the transferred wafer, a laser measurement unit installed on a portion of the second vision module and composed of a laser measurement element and a sensor head so as to measure bending deformation of a wafer transferred after the internal inspection, and a second discharge unit, a first end of which is coupled to a hinge axis in a longitudinal direction of the conveyor and which is downwardly rotated by a predetermined angle around the hinge axis as a center of rotation by way of an operating cylinder installed on a portion of the second discharge unit; an unloading unit implemented as a second conveyor which is located closer to an end portion of the conveyor in a transfer direction thereof and is configured to sequentially transfer wafers having completed the internal inspection; and a control unit configured to control a series of wafer inspection procedures in compliance with sequential control programming.

Furthermore, the present invention provides a wafer inspection apparatus using a linear robot, comprising a conveyor configured to transfer multiple wafers loaded onto a top surface of the conveyor while being rotated at constant speed by power supplied from a motor; a surface inspection unit in which a first vision module is installed to reciprocate in a direction orthogonal to a transfer direction of the conveyor and is configured to perform surface inspection of the wafer; an internal inspection unit which is installed to be spaced apart from the surface inspection unit in the transfer direction of the conveyor and in which a second vision module is installed to reciprocate in a direction orthogonal to the transfer direction of the conveyor and is configured to inspect an inner part of the wafer; and a control unit configured to control a series of wafer inspection procedures in accordance with sequential control programming, In this case, the surface inspection unit may comprise a linear robot including a base frame installed in a direction orthogonal to the transfer direction of the conveyor, a lead screw, a first end of which is coupled to a motor in the base frame and a second end of which is rotatably installed through bearing connection, and a transfer table screw-coupled to the lead screw and configured to reciprocate; and a first vision module including a camera fixedly installed on the transfer table and surface inspection Light Emitting Diodes (LEDs) installed on both ends of the camera.

Further, the internal inspection unit may comprise a linear robot including a base frame installed in a direction orthogonal to the transfer direction of the conveyor, a lead screw, a first end of which is coupled to a motor in the base frame and a second end of which is rotatably installed through bearing connection, and a transfer table screw-coupled to the lead screw and configured to reciprocate; and a second vision module including a camera fixedly installed on the transfer table and an internal inspection Infrared (IR) lighting element installed below the conveyor to correspond to the camera.

Preferably, the cameras installed in the first vision module and the second vision module may be either Charge-Coupled Device (CCD) cameras or line scan cameras.

Preferably, the conveyor for which the second vision module is installed may have a separation space formed therein so that the camera and the internal inspection IR lighting element can see through the wafer.

Preferably the wafer inspection apparatus may further comprise a wafer transfer robot provided above or beside the conveyor so as to adsorb a wafer determined to be defective as a result of the surface or internal inspection of the wafer, and transfer the wafer to an outside of the conveyor.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF SPECIFIC EMBODIMENTS

Figure 1:
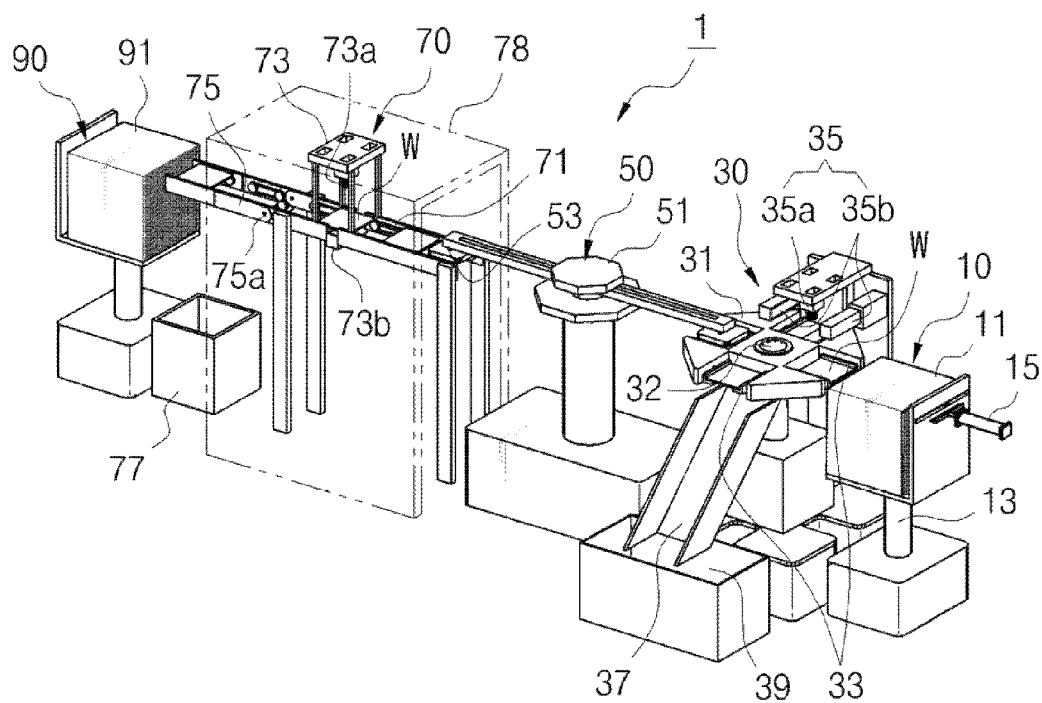
FIG. 1 is a view showing a first embodiment of a wafer inspection apparatus according to the present invention.

Hereinafter, constructions and operations of embodiments of the present invention will be described in detail with reference to the attached drawings.

Reference now should be made to the drawings, in which the same reference numerals are used throughout the different drawings to designate the same or similar components.

Figure 2:
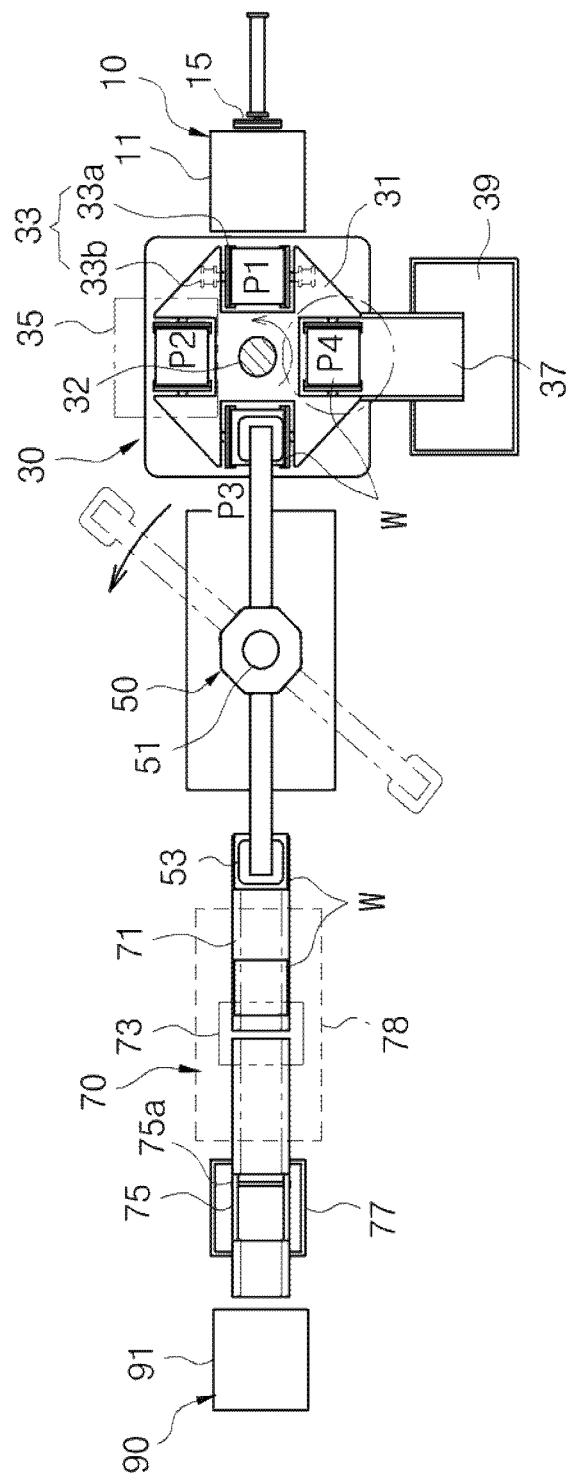
FIG. 2 is a plan view showing the wafer inspection apparatus according to the present invention.
Figure 3:
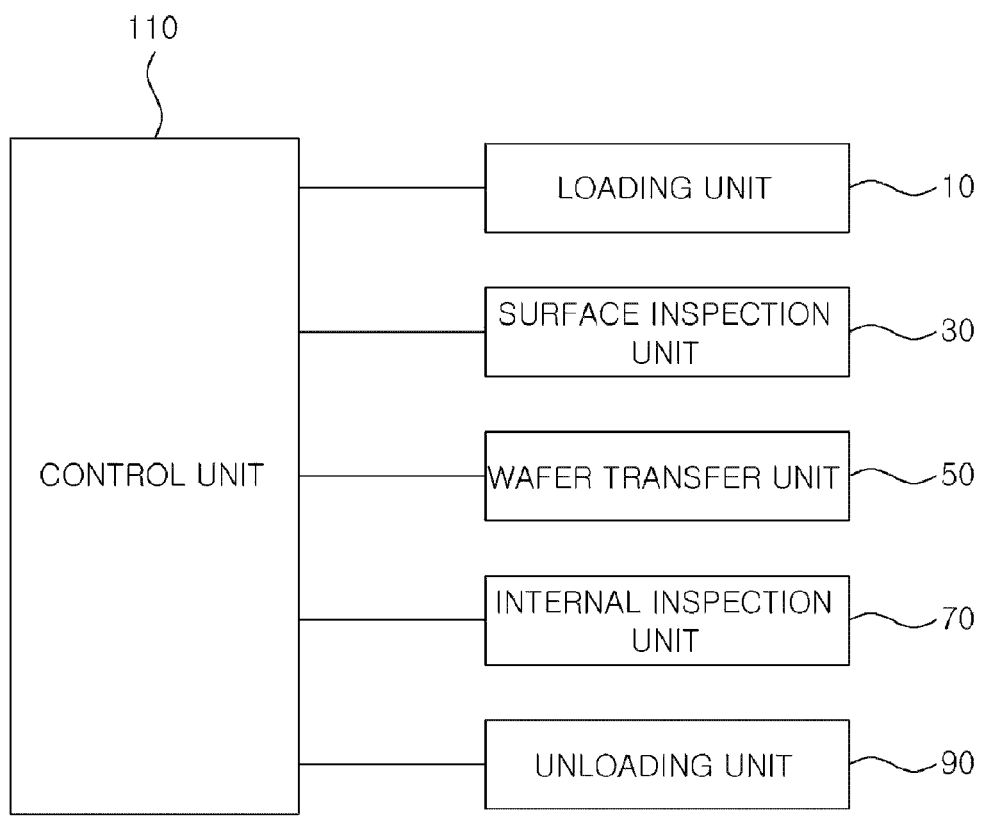
FIG. 3 is a block diagram showing the overall construction of the wafer inspection apparatus according to the present invention.
Figure 4:
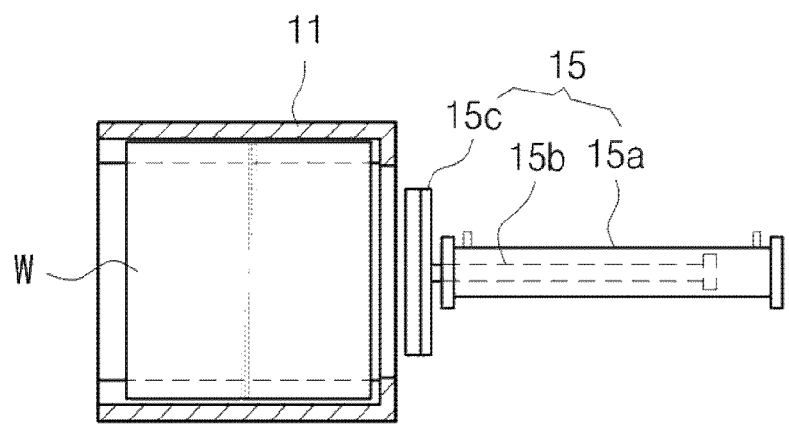
FIG. 4 is a view showing the operating status of a loading unit according to the present invention.
Figure 4:
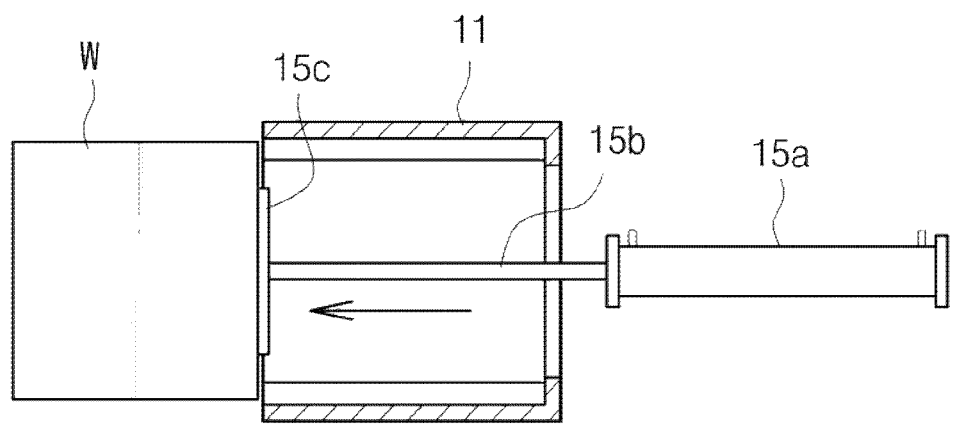
Figure 5:
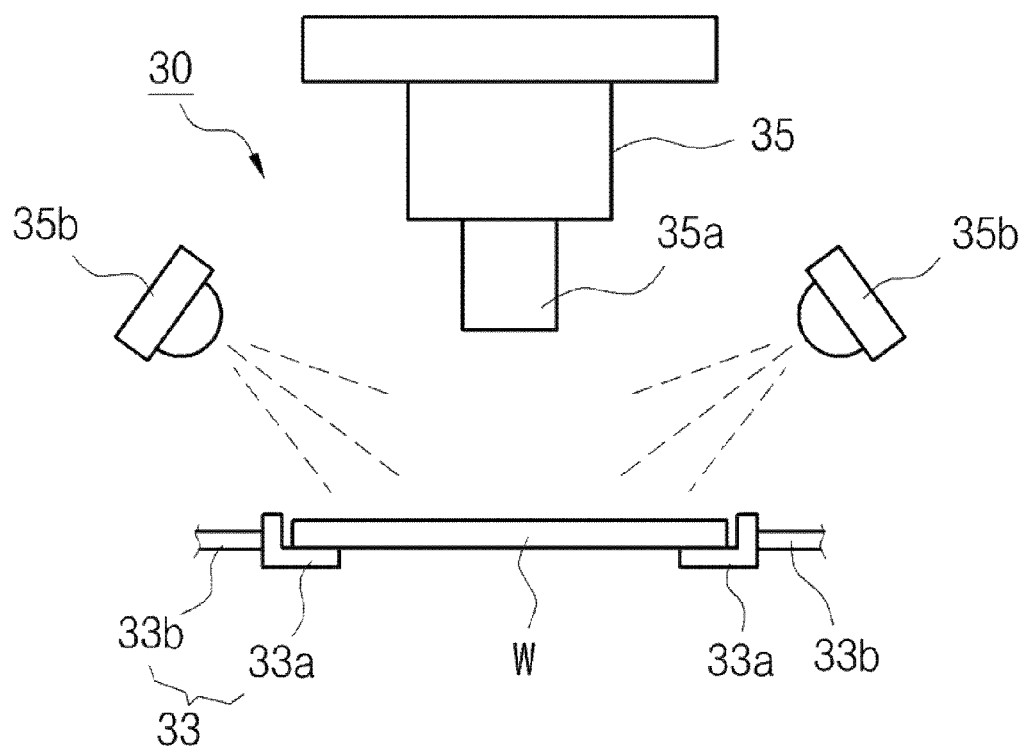
FIG. 5 is a side view showing a surface inspection unit according to the present invention.

FIG. 1 is a view showing a first embodiment of a wafer inspection apparatus according to the present invention, FIG. 2 is a plan view of the wafer inspection apparatus, FIG. 3 is a block diagram showing the overall construction of the wafer inspection apparatus, FIG. 4 is a view showing the operating status of a loading unit, and FIG. 5 is a side view of a surface inspection unit.

Referring to FIGS. 1 to 5, a wafer inspection apparatus 1 according to a first embodiment of the present invention includes a lading unit 10, a surface inspection unit 30, a wafer transfer unit 50, an internal inspection unit 70, an unloading unit 90, and a control unit 110.

Individual components of the present invention will be described in detail below.

The loading unit 10 is configured to sequentially withdraw wafers W loaded in a cassette 11 from the cassette 11 one by one so as to perform the process of inspecting the wafers W. The loading unit 10 includes the cassette 11 having multiple wafers W loaded therein, an elevator 13 for lifting up or lowering the cassette 11, and a push means 15 fixedly installed on a portion of the cassette 11 to be forwardly and backwardly movable in a horizontal direction and configured to push the wafers W loaded in the cassette 11 one by one.

Here, the elevator 13 allows each target wafer W loaded in the cassette 11 to be located on the same plane horizontal to that of a stage 33 which will be described later so that the loaded wafer W can be loaded onto the stage 33.

The push means 15 includes an air cylinder 15a using air pressure, and a push rod 15b coupled to the inside of the air cylinder 15a to be forwardly and backwardly movable and provided with a horizontal reciprocating element 15c coupled to a front end of the push rod 15b. The push means 15 is operated such that as the horizontal reciprocating element 15c moves forwardly and backwardly, it horizontally pushes the wafer W loaded in the cassette 11, thus enabling the wafer W to be withdrawn from the cassette 11.

As shown in FIG. 5, the surface inspection unit 30 functions to sequentially perform surface inspections such as inspection for scratches, breakage, and contamination on the surface of each wafer W loaded from the loading unit 10, and classify the wafer W depending on whether the wafer W is defective or not.

Such a surface inspection unit 30 includes a rotatable table 31, a first vision module 35, and a first discharge unit 37. The rotatable table 31 is installed to be rotatable by power supplied from a motor (not shown) and is provided with at least four stages 33 installed to be spaced apart from one other by a predetermined angle (90°) around a shaft 32 so that wafers W can be loaded onto the top surfaces of the stages 33. The first vision module 35 includes a camera 35a fixedly located above the rotatable table 31 independent of the rotatable table 31 so as to inspect the surfaces of the wafers W, and surface inspection lighting elements (Light Emitting Diodes: LEDs) 35b installed on both sides of the camera 35a. The first discharge unit 37 is formed to be downwardly inclined below the stages 33 so that wafers W determined to be defective as a result of the inspection of the wafers W performed by the first vision module 35 can be separately discharged.

In this case, detection sensors 33c are installed on supports 33a to detect whether a wafer W has been loaded.

Figure 6:
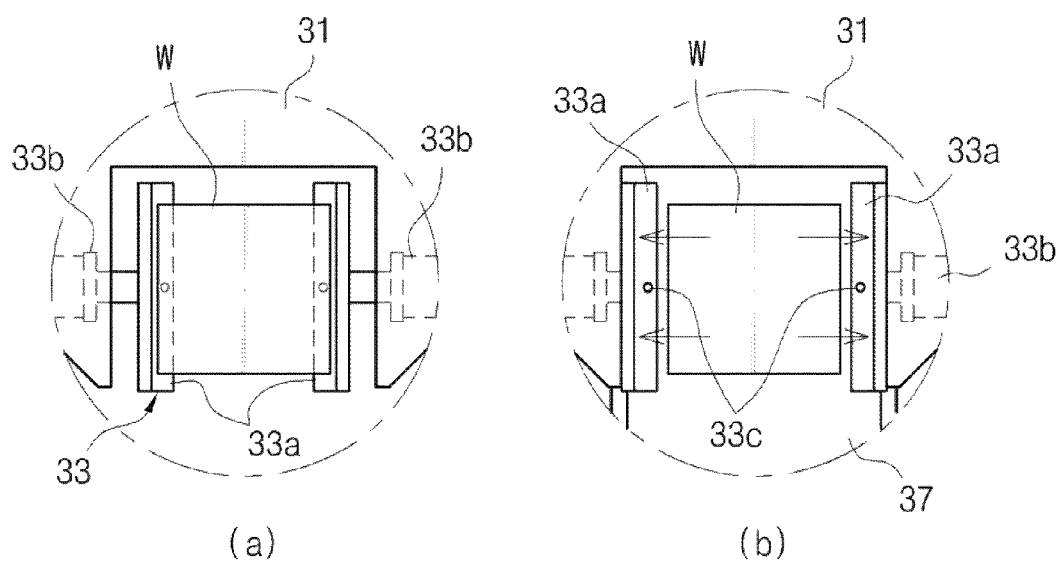
FIG. 6 is a plan view showing the operating status of a stage according to the present invention.

Further, as shown in FIG. 6, each of the stages 33 is implemented as a structure in which the supports 33a installed to be movable away from each other in opposite directions by the operation of air cylinders 33b support both ends of each wafer W. Therefore, when defective wafers need to be separately discharged through the first discharge unit 37, the air cylinders 33b are operated, so that the supports 33a are moved away from each other in opposite directions, thus enabling the wafers W to be discharged into a receiving part 39.

For reference, the rotatable table 31 can be replaced with other rotatable tables in which stages 33 having different sizes are installed depending on the sizes of inspection target wafers W, and then the other rotatable tables can be used.

The wafer transfer unit 50 functions to adsorptively fix the top surfaces of wafers W having completed the surface inspection by the surface inspection unit 30, that is, wafers determined to be non-defective in the surface inspection, and to transfer the wafers W to a subsequent process.

Such a wafer transfer unit 50 has a center portion 51 coupled to be rotatable by power supplied from a motor (not shown), is installed to be lifted up or lowered by an air pressure cylinder (not shown), and is provided with adsorption parts 53 at both ends of the wafer transfer unit 50 to adsorptively fix wafers W using vacuum.

Figure 7:
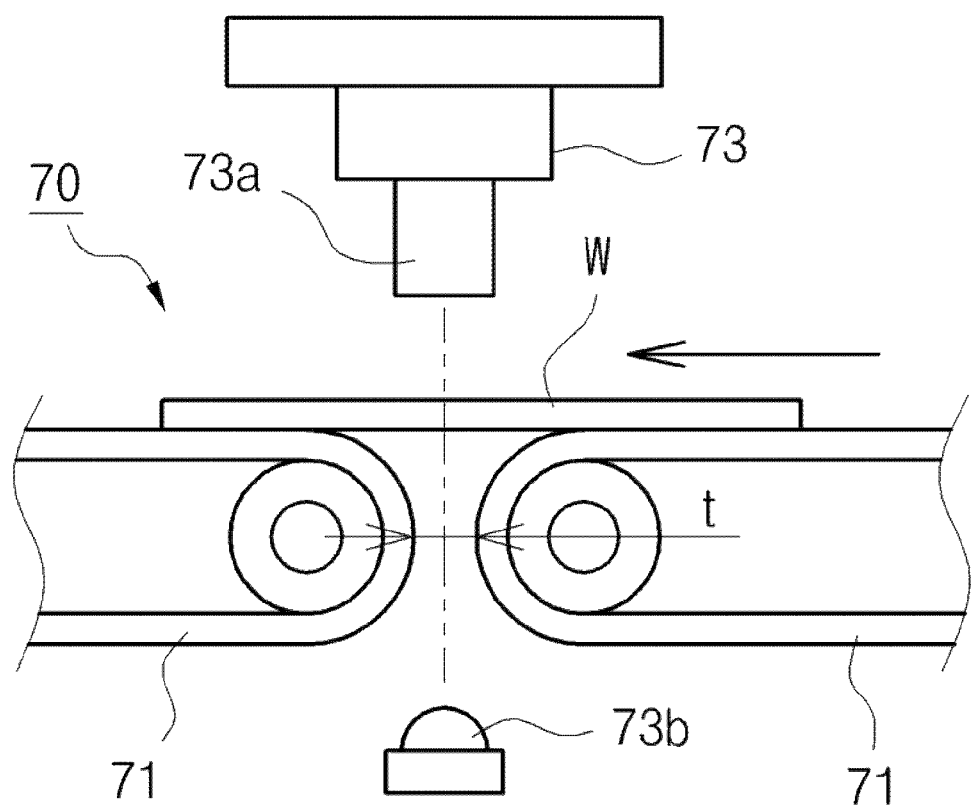
FIG. 7 is a side view showing an internal inspection unit according to the present invention.

As shown in FIG. 7, the internal inspection unit 70 functions to sequentially perform internal inspections such as for cracks, voids, etc. of the inner part of each wafer W transferred by the wafer transfer unit 50, and to classify the wafer W depending on whether the wafer W is defective or not.

Such an internal inspection unit 70 includes a conveyor 71 supplied with power from a motor (not shown) and configured to rotatably transfer the wafer W, transferred by the wafer transfer unit 50, in one direction, and a second vision module 73 configured such that a camera 73a and an internal inspection lighting element (IR lighting element) 73b are respectively installed above and below the conveyor 71 to perform internal inspection of the transferred wafer W.

In this case, the internal inspection unit 70 is installed inside a blackout curtain 78. That is, unlike the surface inspection unit 30, the internal inspection unit 70 can maximize inspection conditions and results only when the internal inspection unit 70 is darkened by shutting out incoming light.

Further, in a portion of the conveyor 71 installed inside the second vision module 73, a predetermined separation space t must be formed. That is, if the conveyor 71 is installed to block the space between the camera 73a and the internal inspection lighting element 73b, the camera 73a cannot see through a wafer W, thus making it impossible to perform internal inspection itself. Therefore, the conveyor 71 is installed as a structure composed of two separate parts so that the predetermined space t can be formed between the camera 73a and the internal inspection lighting element 73b.

Figure 8:
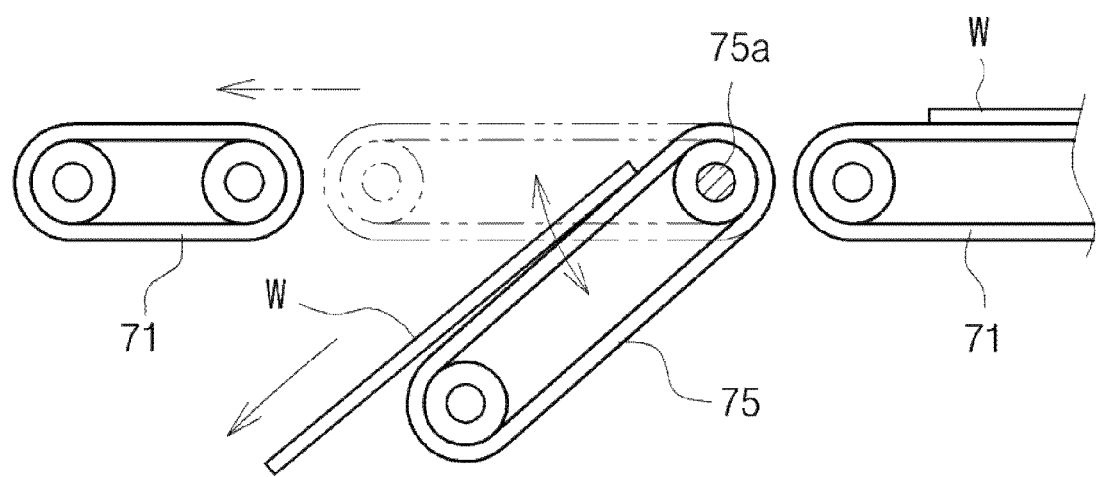
FIG. 8 is a side view showing the state in which a defective wafer is separately discharged by the internal inspection unit according to the present invention.

Furthermore, referring to FIG. 8, a second discharge unit 75 is provided on the conveyor 71 so that a wafer W determined to be defective as a result of the inspection by the second vision module 73 is separately discharged. The second discharge unit 75 is successively installed along the longitudinal direction of the conveyor 71 and is configured to be downwardly rotatable with one end of the second discharge unit 75 coupled to a hinge axis 75a. On a portion of the second discharge unit 75, an operating cylinder (not shown) for downwardly rotating the second discharge unit 75 by a predetermined angle around the hinge axis 75a as a center of rotation is provided.

The unloading unit 90 is located closer to the end of the conveyor 71 in the transfer direction, and includes a cassette 91 lifted up or lowered by the elevator 93 to allow wafers W having completed the internal inspection to sequentially enter and be loaded onto the cassette 91. In this case, wafer detection sensors (not shown) are respectively provided in internal slots of the cassette 91 and are configured not only to detect whether wafers W have been loaded, but also to adjust the height of the cassette 91, thus enabling the wafers W which are sequentially transferred along the conveyor 71 to be smoothly loaded onto the cassette 91.

The control unit 110 controls a series of wafer W inspection and transfer procedures such as by determining whether wafers W are defective while comparing previously input data with measured values and by transferring the wafers W in compliance with sequential control programming during the surface and internal inspections of the wafers W.

Next, a process of inspecting wafers according to the present invention having the above construction will be described in detail.

First, when a wafer W is loaded from the loading unit 10 onto a stage 33 located at position P1 among a plurality of stages 33 installed on the rotatable table 31, the wafer W is located at position P2 while the rotatable table 31 is rotated counterclockwise at an angle of 90°.

In this case, at the same time that the wafer W loaded first onto the stage 33 is rotatably transferred from position P1 to position P2, a second wafer W is loaded onto the stage 33 at position P1, and such loading of wafers W is consecutively performed.

Further, surface inspection of the loaded wafer W is performed by the first vision module 35 installed at position P2.

A wafer W determined to have no defects in the surface inspection is transferred from position P3 to the internal inspection unit 70, which will conduct a subsequent process, by the wafer transfer unit 50 which will be described later.

A wafer W determined to be defective in the surface inspection is separately discharged to the receiving part 39 below the first discharge unit 37 through the first discharge unit 37 while the supports 33 are moved away from each other in opposite directions after the stage 33 has been rotatably transferred to position P4.

Meanwhile, the wafer W having transferred to the internal inspection unit 70 is transferred along the conveyor 71, and undergoes an internal inspection while passing through the second vision module 73.

Wafers W determined to have no defects as a result of the internal inspection by the second vision module 73 are continuously transferred to the end of the conveyor 71, and are then sequentially loaded onto the cassette 91 of the unloading unit 90.

However, wafers W determined to be defective as a result of the inspection by the second vision module 73 are separately discharged to the receiving part 77 provided below the second discharge unit 75 while the second discharge unit 75 is downwardly rotating.

Figure 9:
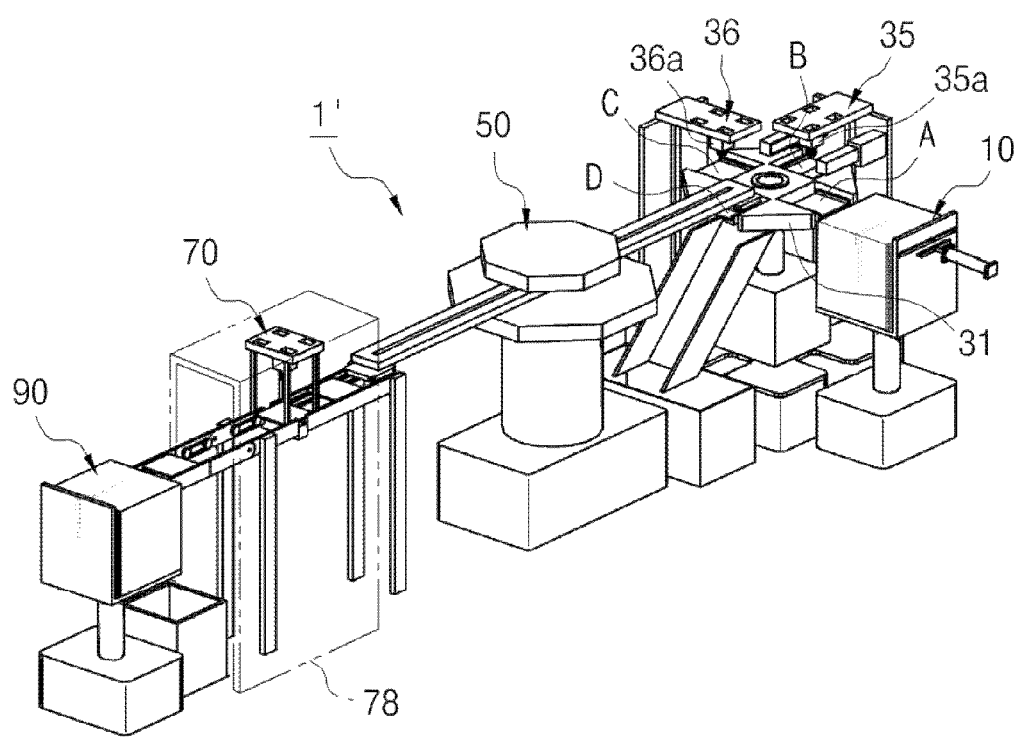
FIG. 9 is a view showing a second embodiment of a wafer inspection apparatus according to the present invention.
Figure 10:
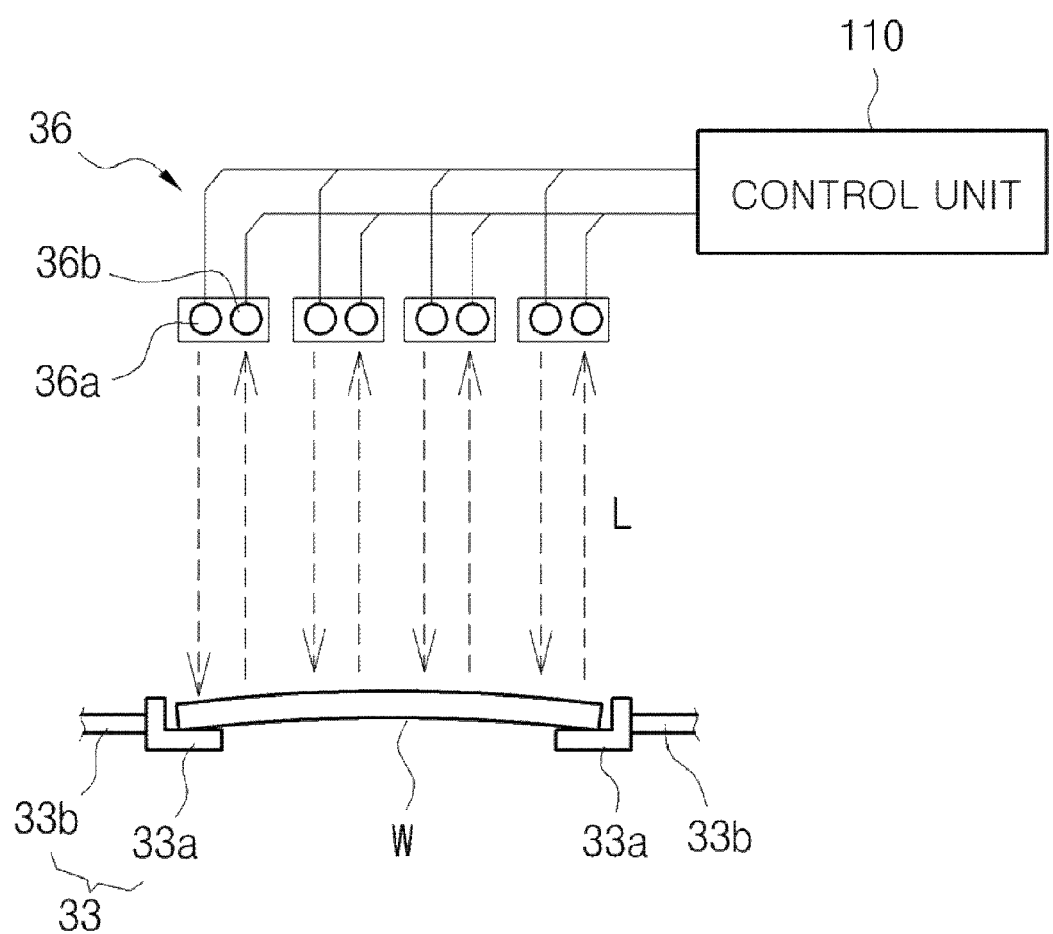
FIG. 10 is a plan view showing the surface inspection unit of FIG. 9.

FIG. 9 is a diagram showing a second embodiment of a wafer inspection apparatus according to the present invention, and FIG. 10 is a plan view showing the surface inspection unit of FIG. 9.

Referring to FIG. 9, the surface inspection unit 30 of a wafer inspection apparatus 1' according to a second embodiment of the present invention further includes a laser measurement unit 36 for measuring the bending deformation degree of a wafer W loaded onto a stage 33. The laser measurement unit 36 includes laser measurement elements 36a installed to be perpendicular to the wafer W and configured to radiate laser beams onto the wafer W, and sensor heads 36b to which the radiated laser beams return.

Such a laser measurement unit 36 is located adjacent to the first vision module 35 of the rotatable table 31 and configured to measure the bending deformation degree of a wafer W which has completed the surface inspection by the first vision module 35 and has been rotatably transferred counterclockwise. That is, as shown in FIG. 10, the distances L relative to the times taken for laser beams to return to the sensor heads 36b from the wafer W after being radiated onto the wafer W by the laser measurement elements 36a are calculated, and then measured values are obtained. The control unit 110 compares the measured values with preset reference values, thus determining whether bending deformation has occurred on the wafer W loaded onto the stage 33.

In the surface inspection unit 30 to which the above-described laser measurement unit 36 is added, the rotatable table 31 starts to gradually rotate counterclockwise by an angle of 90° when a first wafer W is loaded at position A, as shown in FIG. 9. In this case, the wafer W undergoes surface inspection and bending deformation inspection while sequentially passing through positions B and C. A wafer W determined to have no defects as a result of the inspections is transferred from position D by the wafer transfer unit 50 to the internal inspection unit 70 which will conduct a subsequent process, and thereafter undergoes the same process as that of the first embodiment.

However, a wafer W determined to be defective as a result of the surface inspection and the bending deformation inspection is separately discharged to the receiving part 39 below the first discharge unit 37 through the first discharge unit 37 while the supports 33a of the stage 33 are moved away from each other in opposite directions at position D.

Figure 11:
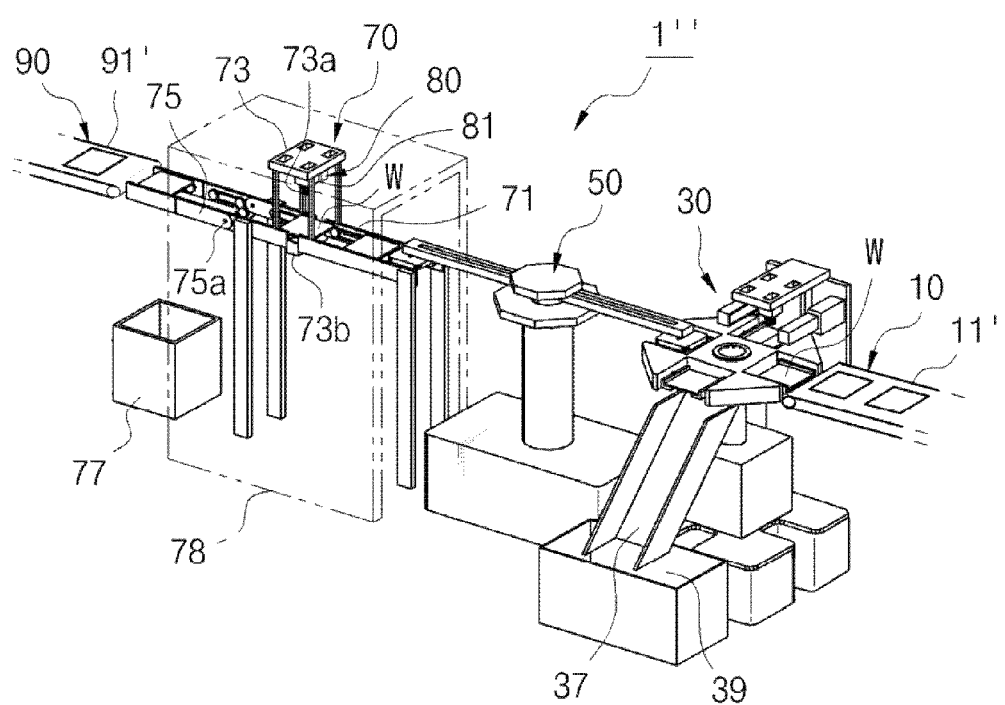
FIG. 11 is a view showing a third embodiment of a wafer inspection apparatus according to the present invention.
Figure 12:
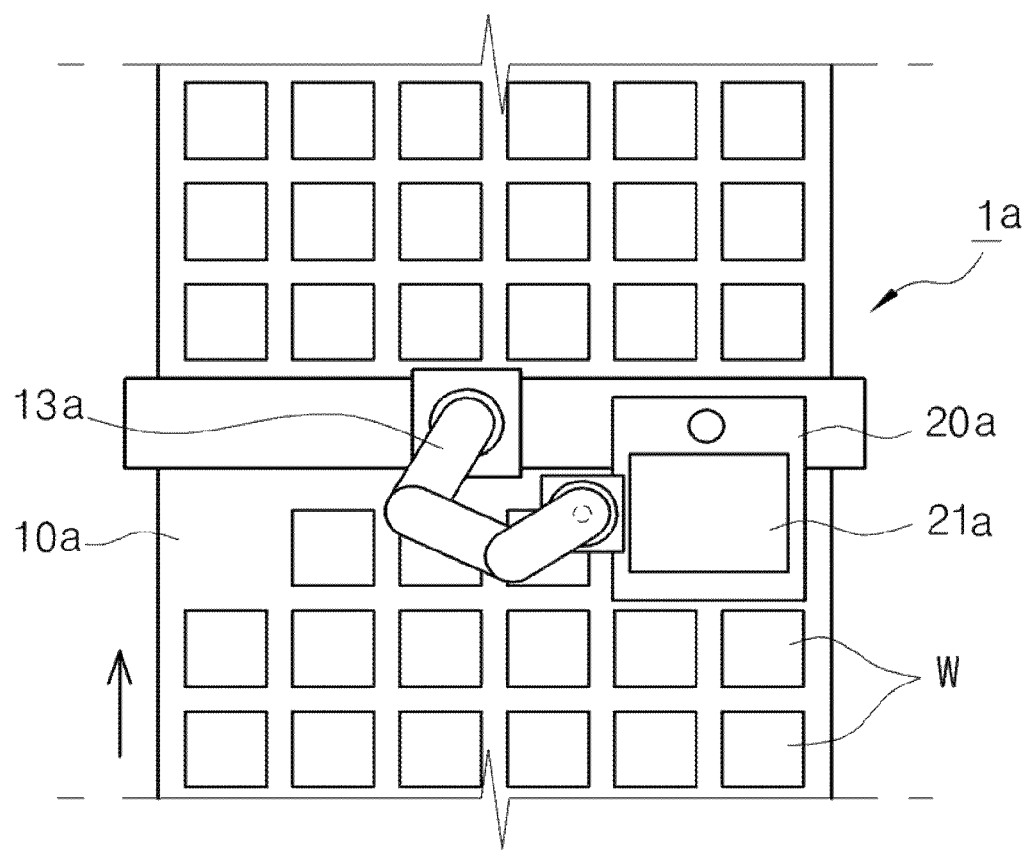
FIG. 12 is a plan view showing the structure of a conventional wafer inspection apparatus.

FIG. 11 is a view showing a third embodiment of a wafer inspection apparatus according to the present invention.

Referring to FIG. 11, in a wafer inspection apparatus 1" according to a third embodiment of the present invention, the constructions of a surface inspection unit 30 and a wafer transfer unit 50 are identical to those of the first embodiment.

In this case, in the internal inspection unit 70 of the wafer inspection apparatus 1", a conveyor 71 is installed to be rotated by power supplied from a motor (not shown) so that a wafer W transferred by the wafer transfer unit 50 can be transferred. The internal inspection unit 70 includes a second vision module 73, a laser measurement unit 80, and a second discharge unit 75. The second vision module 73 is installed above and below the conveyor 71 to perform internal inspection of the transferred wafer W. The laser measurement unit 80 is installed on a portion of the second vision module 73 and provided with laser measurement elements 81 capable of measuring the bending deformation of a wafer W transferred after the completion of the internal inspection. The second discharge unit 75 (refer to FIG. 8) has one end coupled to a hinge axis 75a in the longitudinal direction of the conveyor 71, and is downwardly rotated by a predetermined angle around the hinge axis 75a as a center of rotation by way of an operating cylinder (not shown) installed on a portion of the second discharge unit.

Further, the loading unit 10 and the unloading unit 90 may be implemented as a first conveyor 11' and a second conveyor 91', respectively.

That is, as a wafer W having completed its previous process in the existing line is immediately transferred along the first conveyor 11' of the loading unit 10, the surface inspection and internal inspection of the wafer W are efficiently performed within a short period of time.

Thereafter, the wafer W having completed the internal inspection is transferred to a subsequent process by the second conveyor 91' located closer to the end of the conveyor 71.

Figure 13:
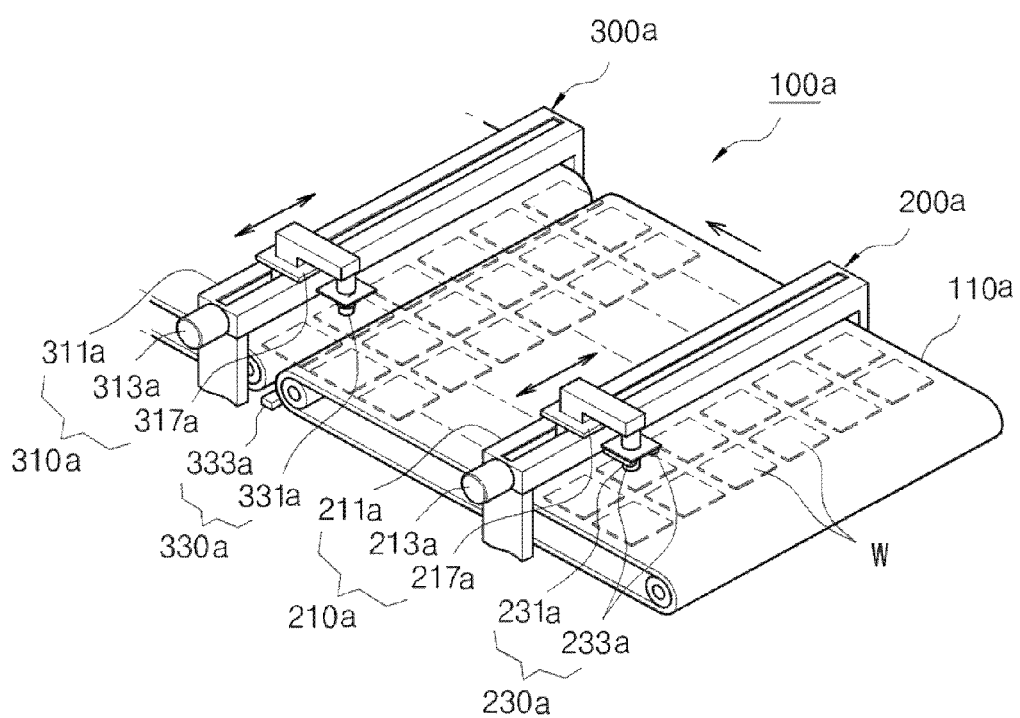
FIG. 13 is a perspective view showing a wafer inspection apparatus according to a fourth embodiment of the present invention.
Figure 14:
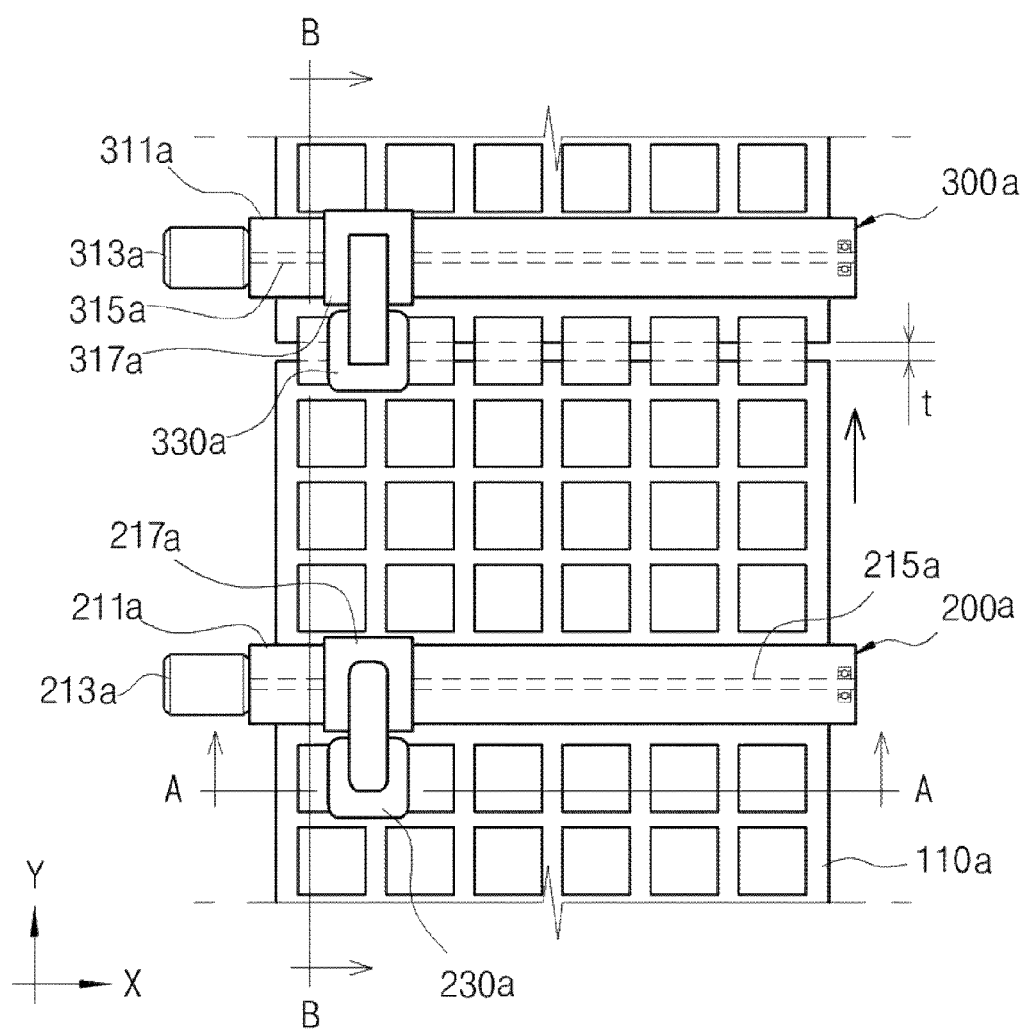
FIG. 14 is a plan view showing the wafer inspection apparatus according to the fourth embodiment of the present invention.
Figure 15:
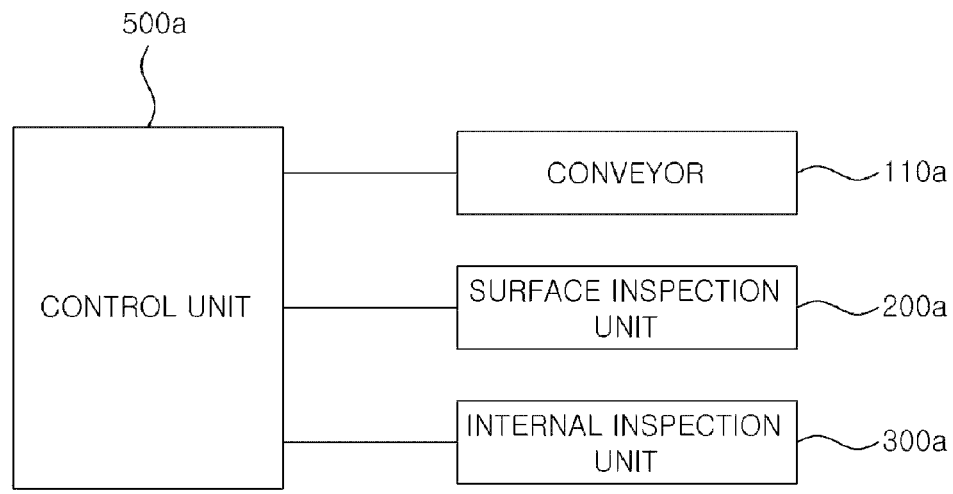
FIG. 15 is a block diagram showing the overall construction of the wafer inspection apparatus according to the fourth embodiment of the present invention.

FIG. 13 is a perspective view showing a wafer inspection apparatus according to a fourth embodiment of the present invention, FIG. 14 is a plan view of the wafer inspection apparatus according to the fourth embodiment of the present invention, and FIG. 15 is a block diagram showing the overall construction of the wafer inspection apparatus according to the fourth embodiment of the present invention.

Referring to FIGS. 13 to 15, a wafer inspection apparatus 100a according to a fourth embodiment of the present invention includes a conveyor 110a, a surface inspection unit 200a, an internal inspection unit 300a, and a control unit 500a.

The construction of the present invention will be described in detail below.

The conveyor 110a is rotated at constant speed by power supplied from a motor (not shown). Such a conveyor 110a allows multiple wafers W loaded onto the top surface of the conveyor 110a to be transferred by a wafer transfer robot (not shown).

The surface inspection unit 200a is configured to sequentially inspect the surfaces of the wafers W transferred along the conveyor 110a, and includes a linear robot 210a and a first vision module 230a.

In this case, the linear robot 210a includes a base frame 211a installed in a direction orthogonal to the transfer direction of the conveyor 110a, a lead screw 215a, one end of which is connected to a motor 213a in the base frame 211a and the other end of which is rotatably installed through bearing connection, and a transfer table 217a screw-coupled to the lead screw 215a and configured to reciprocate.

Figure 16:
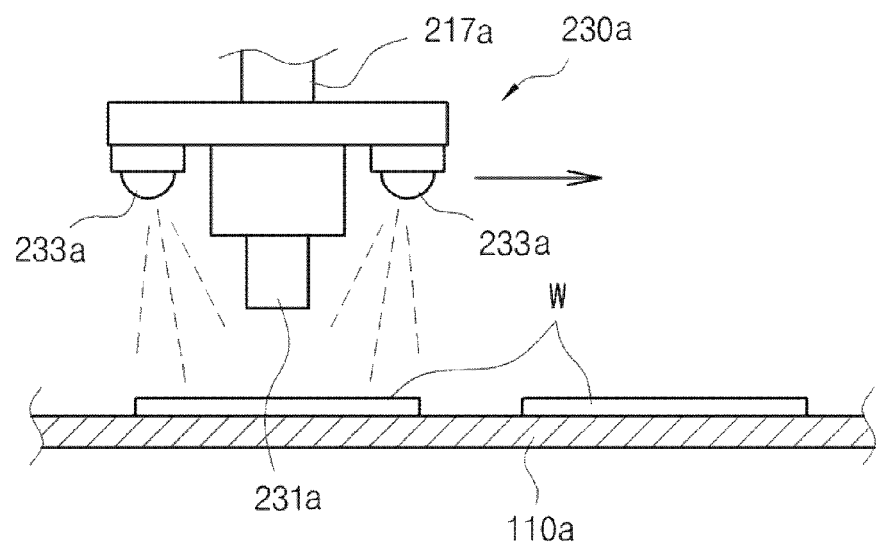
FIG. 16 is a sectional view taken along line A-A of FIG. 14.

Further, as shown in FIG. 16, the first vision module 230a includes a camera 231a fixedly installed on the transfer table 217a and surface inspection lighting elements (LEDs) 233a installed on both sides of the camera 231a, and inspects scratches, breakage, contamination, etc. on surfaces of wafers W transferred by the conveyor 110a.

The internal inspection unit 300a is installed to be spaced apart from the surface inspection unit 200a by a predetermined distance in a direction behind the surface inspection unit 200a, that is, in the transfer direction of the conveyor 110a, and is configured to sequentially inspect the inner parts of the wafers W transferred after the inspection thereof has been completed by the surface inspection unit 200a. The internal inspection unit 300a includes a linear robot 310a and a second vision module 330a.

In this case, the linear robot 310a includes a base frame 311a installed in a direction orthogonal to the transfer direction of the conveyor 110a, a lead screw 315a, one end of which is connected to a motor 313a in the base frame 311a and the other end of which is rotatably installed through bearing connection, and a transfer table 317a screw-coupled to the lead screw 315a and configured to reciprocate.

Figure 17:
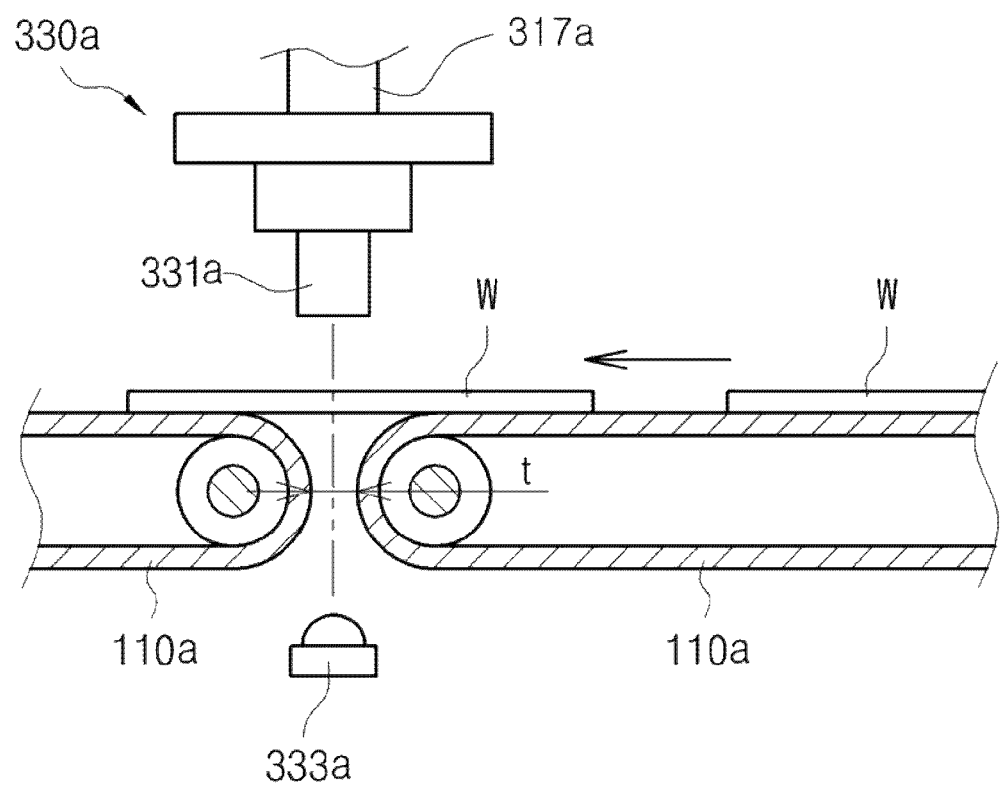
FIG. 17 is a sectional view taken along line B-B of FIG. 14.

Further, as shown in FIG. 17, the second vision module 330a includes a camera 331a fixedly installed on the transfer table 317a, and an internal inspection lighting element (IR lighting element) 333a located below the conveyor 110a to correspond to the camera 331a, and then inspects the inner parts of wafers W for cracks, voids, etc.

In this case, predetermined separation space t is formed in the conveyor 110a in which the internal inspection of wafers W is performed by the second vision module 330a. That is, if the conveyor 110a is installed to block the space between the camera 331a and the internal inspection lighting element 333a, the camera 331a cannot see through a wafer W, thus making it impossible to perform the internal inspection itself. Therefore, the conveyor 110a is installed as a structure composed of two equal parts so that the predetermined space t can be formed between the camera 331a and the internal inspection lighting element 333a.

Meanwhile, the cameras 231a and 331a used for the first and second vision modules 230a and 330a are implemented as either Charge-Coupled Device (CCD) Cameras or line scan cameras.

In this case, when the cameras 231a and 331a are implemented as CCD cameras, the conveyor 110a is operated to repeat transferring and stopping. That is, while the CCD cameras inspect each loaded wafer W while repeating movement and stopping, the conveyor 110a temporarily stops. Thereafter, when the inspection of the wafer W has been completed, the conveyor 110a restarts to operate and then transfers a subsequently loaded wafer W to an inspection position.

Further, when the cameras 231a and 331a are implemented as line scan cameras, the conveyor 110a continuously to move at constant speed without stopping. That is, while the line scan cameras rapidly move in accordance with the transfer speed of the wafer W, they inspect the wafer W. That is, the conveyor 110a and the line scan cameras inspect wafers W while continuously moving without stopping.

The control unit 500a controls a series of wafer W transfer and inspection procedures such as by determining whether wafers W are defective while comparing previously input data with measured values during the surface and internal inspections of the wafers W, and by transferring the wafers W in compliance with sequential control programming.

Meanwhile, a separate wafer transfer robot R (refer to FIG. 18), capable of adsorbing wafers W, which are determined to be defective as a result of the inspection by the surface inspection unit 200a or the internal inspection unit 300a and externally transferring the adsorbed wafers W, is provided above or beside the conveyor 110a.

Figure 18:
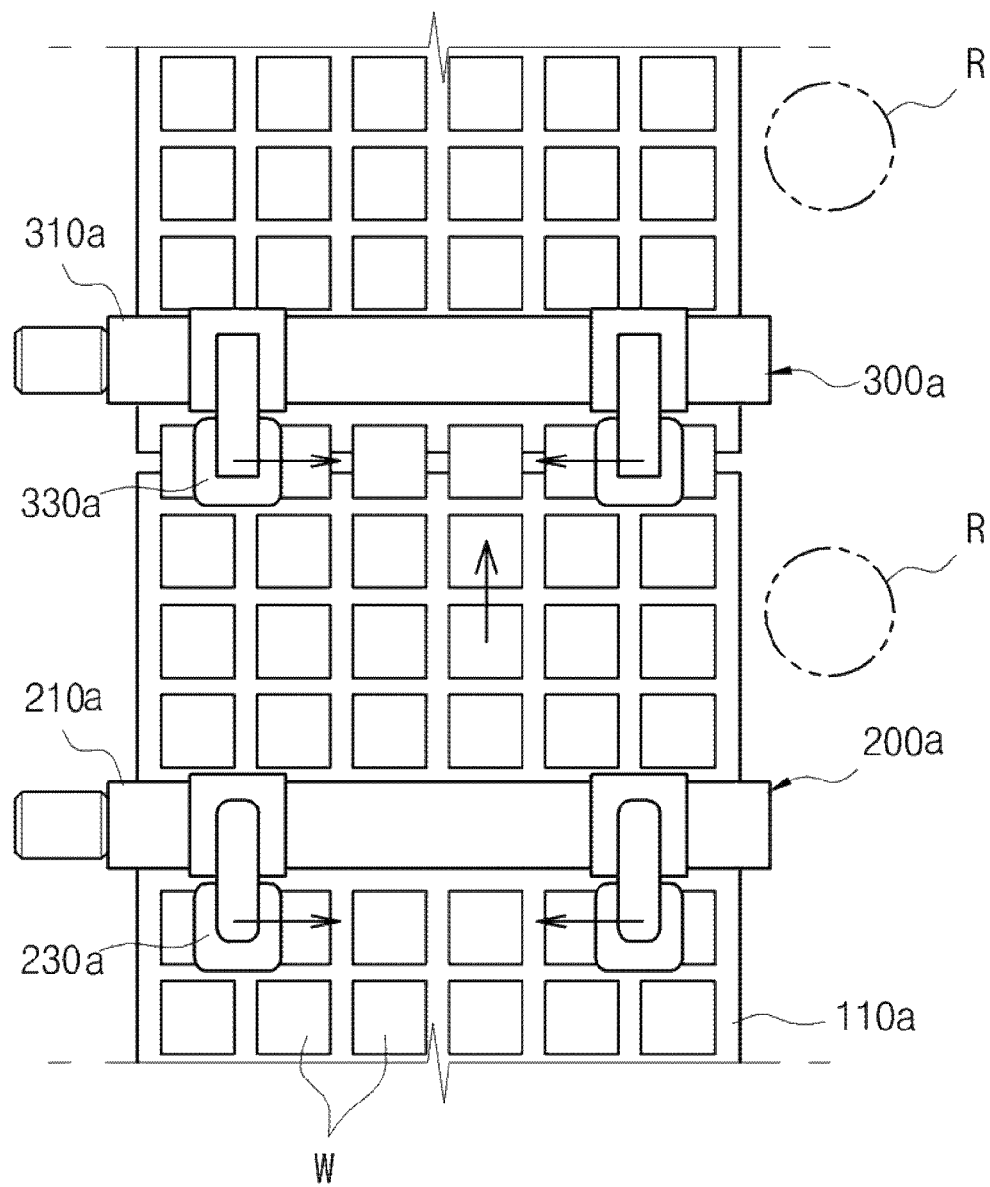
FIG. 18 is a view showing a fifth embodiment of a wafer inspection apparatus according to the present invention.

FIG. 18 is a view showing a fifth embodiment of a wafer inspection apparatus according to the present invention.

Referring to FIG. 18, two first vision modules 230a and two second vision modules 330a are respectively installed on the linear robots 210a and 310a.

Therefore, when surface or internal inspection of each wafer W transferred by the conveyor 110a is performed, the first and second vision modules 230a and 330a, each being installed as two modules, perform inspections while simultaneously moving to the center from one side or opposite sides, thus reducing the time required for the inspection of the wafers W.

Hereinafter, a process of inspecting wafers according to the present invention having the above construction will be described.

First, at the same time that multiple wafers W loaded onto the conveyor 110a and transferred in one direction are located on the surface inspection unit 200a, the first vision modules 230a are moving in a direction orthogonal to the transfer direction of the conveyor 110a, thus performing surface inspection of the wafers W.

Wafers W having completed the surface inspection are located in the internal inspection unit 300a, installed to be spaced apart from the surface inspection unit 200a in the direction behind the surface inspection unit 200a, while being continuously transferred by the conveyor 110a. The second vision modules 330a perform internal inspection of the wafers W while moving in a direction orthogonal to the transfer direction of the conveyor 110a.

In this case, the control unit 500a determines whether wafers W are defective while comparing previously input data with measured values, and picks wafers W, determined to be defective as a result of the inspection by the surface inspection unit 200a or the internal inspection unit 300a, out of the conveyor by controlling separate wafer transfer robots R.

Wafers W determined not to be defective as a result of the inspections by the surface inspection unit 200a and the internal inspection unit 300a are continuously transferred by the conveyor 110a, and are then loaded onto the cassette by the wafer transfer robots.

Meanwhile, although the wafer inspection apparatus according to the present invention has been exemplarily shown and described to be used for surface and internal inspections of wafers (solar cells), the present invention is not limited to those embodiments and may also be used for the surface and internal inspections of camera lenses for mobile phones, digital cameras, and Closed Circuit Television (CCTV), lenses for Infrared (IR) cameras (synthetic sapphire), jewelry, etc. Further, those skilled in the art will appreciate that various modifications, additions and substitutions are possible, without departing from the scope and spirit of the invention.

As described above, a wafer inspection apparatus according to the present invention having the above construction is advantageous in that, since surface inspection and internal inspection of wafers are continuously performed using a single apparatus, multiple wafers can be simultaneously processed, thus improving working efficiency, and in that, since an inspection line can be shortened, so that contamination or dust that may occur during the transfer of wafers can be minimized, thus improving a yield.

What is claimed is:

1. A wafer inspection apparatus, comprising:
   a loading unit configured to allow a cassette, in which multiple wafers are loaded, to be lifted up or lowered by an elevator, the loading unit having push means installed on a portion thereof to allow the wafers to be horizontally withdrawn one by one;
   a surface inspection unit provided with a plurality of stages on a top surface thereof so that the wafers withdrawn from the loading unit can be loaded onto the stages, the surface inspection unit performing surface inspection of each of the wafers using a first vision module installed above the stages;
   a wafer transfer unit, a center portion of which is rotatably installed and both ends of which are provided with adsorption parts so as to adsorptively fix a top surface of each wafer having completed the surface inspection and transfer the wafer to a subsequent process;
   an internal inspection unit in which a conveyor that is rotated in one direction by power supplied from a motor is installed to allow the wafer transferred by the wafer transfer unit to be transferred, the internal inspection unit performing internal inspection of the transferred wafer through a second vision module installed above and below the conveyor;
   an unloading unit located closer to an end portion of the conveyor in a transfer direction thereof, and provided with a cassette lifted up or lowered by an elevator, thus enabling wafers having completed the internal inspection to be sequentially loaded onto the unloading unit; and
   a control unit configured to control a series of wafer inspection procedures in compliance with sequential control programming.

2. The wafer inspection apparatus according to claim 1, wherein the push means comprises an air cylinder, and a push rod coupled to inside of the air cylinder to be forwardly and backwardly movable and provided with a horizontal reciprocating element coupled to a front end of the push rod.

3. The wafer inspection apparatus according to claim 1, wherein the surface inspection unit comprises:
   a rotatable table installed to be rotatable by power supplied from the motor, and provided with at least four stages installed to be spaced apart from one another by a predetermined angle around a shaft so that wafers can be loaded onto top surfaces of the stages;

the first vision module including a camera installed above the rotatable table independent of the rotatable table, and surface inspection lighting elements installed on both sides of the camera; and a first discharge unit formed to be downwardly inclined below the stages so that a wafer determined by the first vision module to be defective can be separately discharged.

4. The wafer inspection apparatus according to claim 1, wherein each of the stages comprises supports for supporting both ends of a wafer and an air cylinder for moving the supports away from each other in opposite directions.

5. The wafer inspection apparatus according to claim 1, wherein the internal inspection unit comprises:

the conveyor rotated in one direction by power supplied from a motor so that each wafer transferred by the wafer transfer unit can be transferred;

the second vision module provided with a camera and an internal inspection lighting element respectively installed above and below the conveyor so that internal inspection of the wafer transferred by the conveyor can be performed; and a second discharge unit, a first end of which is coupled to a hinge axis in a longitudinal direction of the conveyor, the second discharge unit being downwardly rotated by a predetermined angle around the hinge axis as a center of rotation by way of an operating cylinder installed on a portion of the second discharge unit.

6. The wafer inspection apparatus according to claim 5, wherein the conveyor for which the second vision module is installed has a predetermined separation space formed therein so that the camera and the internal inspection lighting element can see through the wafer.

7. The wafer inspection apparatus according to claim 5, wherein the internal inspection unit includes a blackout curtain installed therein to shut out incoming light and darken the internal inspection unit.

8. A wafer inspection apparatus, comprising:

a loading unit configured to allow a cassette, in which multiple wafers are loaded, to be lifted up or lowered by an elevator, the loading unit having a push rod installed on a portion thereof to allow the wafers to be horizontally withdrawn one by one;

a surface inspection unit provided with a plurality of stages on a top surface thereof so that the wafers withdrawn from the loading unit can be loaded onto the stages, the surface inspection unit performing bending deformation inspection of each of the wafers while performing surface inspection of the wafer using a first vision module installed above the stages;

a wafer transfer unit, a center portion of which is rotatably installed and both ends of which are provided with adsorption parts so as to adsorptively fix a top surface of each wafer having completed the surface inspection and transfer the wafer to a subsequent process;

an internal inspection unit in which a conveyor, which is rotated in one direction by power supplied from a motor, is installed to allow the wafer transferred by the wafer transfer unit to be transferred, the internal inspection unit performing internal inspection of the transferred wafer through a second vision module installed above and below the conveyor;

an unloading unit located closer to an end portion of the conveyor in a transfer direction thereof, and provided with a cassette lifted up or lowered by an elevator, thus enabling wafers having completed the internal inspection to be sequentially loaded onto the unloading unit; and a control unit configured to control a series of wafer inspection procedures in compliance with sequential control programming.

9. The wafer inspection apparatus according to claim 8, wherein the surface inspection unit comprises:

a rotatable table installed to be rotatable by power supplied from the motor, and provided with at least four stages installed to be spaced apart from one another by a predetermined angle around a shaft so that wafers can be loaded onto top surfaces of the stages;

the first vision module including a camera installed above the rotatable table independent of the rotatable table, and surface inspection lighting elements installed on both sides of the camera;

a laser measurement unit located adjacent to the first vision module, and provided with a laser measurement element, which is installed to be perpendicular to a wafer and is configured to radiate a laser beam onto the wafer, and a sensor head, to which the radiated laser beam returns, thus measuring a bending deformation degree of the wafer; and a first discharge unit formed to be downwardly inclined below the stages so that a wafer determined by the first vision module or the laser measurement unit to be defective can be separately discharged.

10. A wafer inspection apparatus, comprising:

a loading unit configured to allow multiple wafers to be transferred by a first conveyor;

a surface inspection unit provided with a plurality of stages on a top surface thereof so that the wafers transferred by the loading unit can be loaded onto the stages, the surface inspection unit performing surface inspection of each of the wafers using a first vision module installed above the stages;

a wafer transfer unit, a center portion of which is rotatably installed and both ends of which are provided with adsorption parts so as to adsorptively fix a top surface of each wafer having completed the surface inspection and transfer the wafer to a subsequent process;

an internal inspection unit in which a conveyor that is rotated in one direction by power supplied from a motor is installed to allow the wafer transferred by the wafer transfer unit to be transferred, the internal inspection unit including a second vision module installed above and below the conveyor to perform an internal inspection of the transferred wafer, a laser measurement unit installed on a portion of the second vision module and composed of a laser measurement element and a sensor head so as to measure bending deformation of a wafer transferred after the internal inspection, and a second discharge unit, a first end of which is coupled to a hinge axis in a longitudinal direction of the conveyor and which is downwardly rotated by a predetermined angle around the hinge axis as a center of rotation by way of an operating cylinder installed on a portion of the second discharge unit;

an unloading unit implemented as a second conveyor which is located closer to an end portion of the conveyor in a transfer direction thereof and is configured to sequentially transfer wafers having completed the internal inspection; and a control unit configured to control a series of wafer inspection procedures in compliance with sequential control programming.

11. A wafer inspection apparatus using a linear robot, comprising:
- a conveyor configured to transfer multiple wafers loaded onto a top surface of the conveyor while being rotated at constant speed by power supplied from a motor;
- a surface inspection unit in which a first vision module is installed to reciprocate in a direction orthogonal to a transfer direction of the conveyor and is configured to perform surface inspection of the wafer;
- an internal inspection unit which is installed to be spaced apart from the surface inspection unit in the transfer direction of the conveyor and in which a second vision module is installed to reciprocate in a direction orthogonal to the transfer direction of the conveyor and is configured to inspect an inner part of the wafer; and
- a control unit configured to control a series of wafer inspection procedures in accordance with sequential control programming,
- wherein the surface inspection unit comprises a linear robot including a base frame installed in a direction orthogonal to the transfer direction of the conveyor, a lead screw, a first end of which is coupled to a motor in the base frame and a second end of which is rotatably installed through bearing connection, and a transfer table screw-coupled to the lead screw and configured to reciprocate; and a first vision module including a camera fixedly installed on the transfer table and surface inspection Light Emitting Diodes (LEDs) installed on both ends of the camera, and
- wherein the internal inspection unit comprises a linear robot including a base frame installed in a direction orthogonal to the transfer direction of the conveyor, a lead screw, a first end of which is coupled to a motor in the base frame and a second end of which is rotatably installed through bearing connection, and a transfer table screw-coupled to the lead screw and configured to reciprocate; and a second vision module including a camera fixedly installed on the transfer table and an internal inspection Infrared (IR) lighting element installed below the conveyor to correspond to the camera.

12. The wafer inspection apparatus according to claim 11, wherein the cameras installed in the first vision module and the second vision module are either Charge-Coupled Device (CCD) cameras or line scan cameras.

13. The wafer inspection apparatus according to claim 11, wherein the conveyor for which the second vision module is installed has a separation space formed therein so that the camera and the internal inspection IR lighting element can see through the wafer.

14. The wafer inspection apparatus according to claim 11, further comprising a wafer transfer robot provided above or beside the conveyor so as to adsorb a wafer determined to be defective as a result of the surface or internal inspection of the wafer, and transfer the wafer to an outside of the conveyor.

* * * * *